United States Patent [19]
Veriac et al.

[11] Patent Number: 6,114,130
[45] Date of Patent: Sep. 5, 2000

[54] REAGENT FOR MEASUREMENT OF THE HAEMOGLOBIN AND DETERMINATION OF THE LEUKOCYTES IN A BLOOD SAMPLE

[75] Inventors: Sylvie Veriac, Montpellier; Henri Champseix, Montferrier sur Lez, both of France

[73] Assignee: ABX, Montpellier, France

[21] Appl. No.: 09/352,666

[22] Filed: Jul. 9, 1999

[30] Foreign Application Priority Data

Aug. 4, 1998 [FR] France .................................. 98 10010

[51] Int. Cl.[7] .............................. G01N 33/53; C12Q 1/00
[52] U.S. Cl. .................................. 435/7.24; 435/4; 436/66
[58] Field of Search ........................... 435/7.24, 4; 436/66

[56] References Cited

U.S. PATENT DOCUMENTS

| | | | |
|---|---|---|---|
| 4,250,051 | 2/1981 | Armstrong | 435/7.24 |
| 4,529,705 | 7/1985 | Larsen | 435/7.24 |
| 4,751,179 | 6/1988 | Ledis et al. | 435/34 |
| 5,242,832 | 9/1993 | Sakata | 435/7.24 |
| 5,958,781 | 9/1999 | Wong et al. | 435/7.24 |

FOREIGN PATENT DOCUMENTS

| | | |
|---|---|---|
| 0 430 751 A1 | 6/1991 | European Pat. Off. . |
| 0 660 113 A2 | 6/1995 | European Pat. Off. . |
| 0 743 519 A2 | 11/1996 | European Pat. Off. . |
| 2 735 578 | 12/1996 | France . |

*Primary Examiner*—Louise N. Leary
*Attorney, Agent, or Firm*—Pollock, Vande Sande & Amernick

[57] ABSTRACT

A reagent for measurement of the haemoglobin and determination of the leukocytes in a blood sample is provided. This reagent comprises at least one detergent of the cationic type; a compound of the glycoside type, and in particular a saponin; at least one inorganic salt and/or an osmotic and/or leukoprotective agent; and an organic and/or inorganic buffer which can adjust the pH of the agent selectively, either to a substantially neutral value, e.g. pH between 5 and 8, or to a basic value, e.g. pH between 8 and 12. The reagent can be used in haematological analyses in human and veterinary medicine.

14 Claims, 3 Drawing Sheets

REAGENT FOR MEASUREMENT OF THE HAEMOGLOBIN AND DETERMINATION OF THE LEUKOCYTES IN A BLOOD SAMPLE

FIELD OF THE INVENTION

The invention relates to haematological analyses.

More specifically, it relates to a reagent for measurement of the haemoglobin and determination of the leukocytes in a blood sample.

BACKGROUND OF THE INVENTION

Measurement of the concentration of the haemoglobin and determination of the leukocytes in particular of specific leukocytic sub-populations, is of primordial importance in diagnosis of specific pathologies, both in human and veterinary medicine.

Haemoglobin is a chromo-protein which is contained in the red globules (or erythrocytes) of the blood.

Measurement of the concentration of the haemoglobin thus requires use of a cellular lysis reagent, which can carry out lysis of the erythrocytes or red globules, in order to release the haemoglobin, so that the latter can be measured.

For this purpose, it is known to use reagents which contain cyanide ions, which can carry out lysis of the erythrocyte, and transform the haemoglobin into a stable chromogen compound, in order to permit determination of the haemoglobin by means of colorimetry measurement. A reagent of this type is described in particular in U.S. Pat. No. 3,874,852. The main disadvantage of this reagent is that it uses cyanide. In addition, it does not make it possible to identify and quantify the leukocyte sub-populations which are contained in the blood sample to be analysed.

In fact, the determination of leukocyte sub-populations, in particular of lymphocytes, monocytes, neutrophils, and eosinophils, is of primordial importance for identification of specific pathologies.

Various reagents which do not contain cyanide have already been proposed in the prior art, for determination of the leukocytes in a blood sample.

Examples of reagents of this type are described for example in document EP 0 325 710.

Although these reagents have the advantage that they do not use cyanide, they have the disadvantage that they do not permit accurate identification and quantification of the leukocyte sub-populations of the blood.

Thus, the reagent according to EP 0 325 710 makes it possible, for example, to determine the eosinophils which are present in a blood sample, without however making it possible to identify accurately each of the other leukocyte sub-populations.

In addition, document EP 0 424 871 describes reagents which permit differentiation of leukocyte sub-populations. However, these reagents sometimes encounter difficulties in overcoming the membranous resistance which is present in human pathology and in veterinary biology.

The object of the invention is in particular to eliminate the aforementioned disadvantages.

In particular, it aims to provide a haematological analysis reagent for measurement of the haemoglobin and determination of the leukocytes in a blood sample, which in particular permits lysis of the erythrocytes or red globules, as well as measurement of the haemoglobin, without using cyanide compounds.

The object of the invention is also to provide a reagent of this type, which makes it possible to quantify the total leukocytes or white globules, to identify at least one leukocyte sub-population, and to quantify at least one leukocyte sub-population.

The object of the invention is also to provide a reagent of this type which can be used both in human and veterinary medicine.

In addition, the object of the invention is to provide a reagent of this type which can eliminate the analysis problems which are associated with the membranous resistance which is encountered in human pathology and in veterinary biology.

SUMMARY OF THE INVENTION

This invention is directed to a reagent for the measurement of the haemoglobin and determination of the leukocytes in a blood sample, wherein it comprises:

at least one detergent of the cationic type;

a compound of the glycoside type, and in particular a saponin;

at least one inorganic salt and/or an osmotic and/or leuko-protective agent; and an organic and/or inorganic buffer, which can adjust the pH of the reagent selectively, either to a substantially neutral value (pH between 5 and 8), or to a basic value (pH between 8 and 12).

Figure 1:
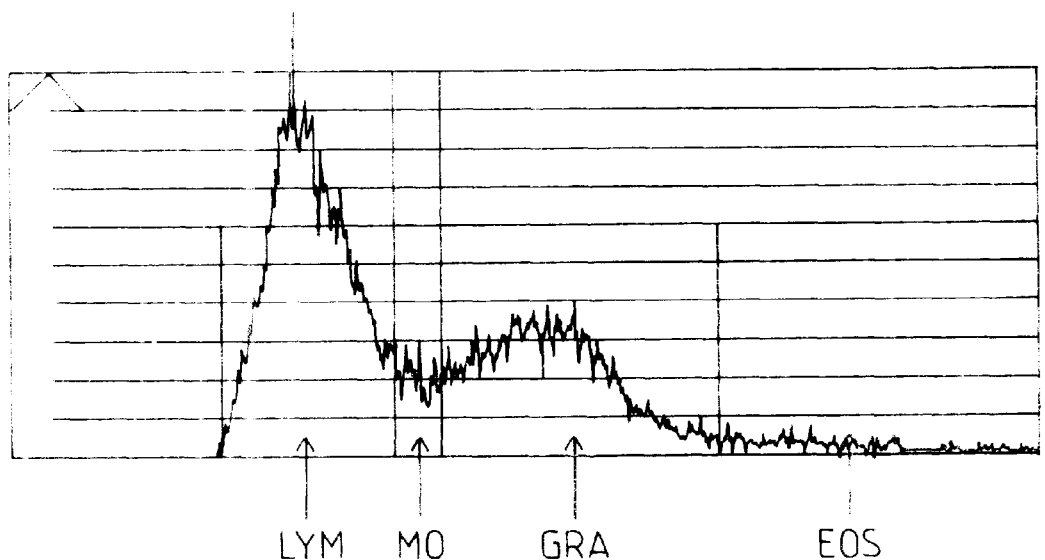
FIGS. 1 and 2 show the number of leukocytes according to a relative intensity in a haematological analysis carried out using an automatic haematology device sold under the name ABX-Micros, made by the French Company ABX.

The FIGS. 3 through 6 relate to a resistive analysis, such that the following sub-populations can be seen from right to left, delimited by arrows; lymphocytes (LYM), monocytes (MO), granulocytes (GRA), and polynuclear eosinophils (EOS).

DETAILED DESCRIPTION OF THE INVENTION

Thus, the haematological reagent according to the invention comprises at least four main components which make it possible to achieve the above-described aims.

The detergent of the cationic type carries out a function of lysis of the red globules or erythrocytes, making it possible to release the haemoglobin, which can then be determined by adsorbance measurement.

The (anionic and cationic) ionic detergents are mainly used to dissociate the proteic complexes, and to solubilize the proteins of the membranes. They are so-called denaturing.

In addition, they have fast and non-specific action on the cell populations of the blood (erythrocytes and leukocytes).

The compound of the glycoside type, and in particular a saponin, contributes towards the lysis of the red globules. In addition, it carries out a function of stabilization relative to the haemoglobin, which makes it possible to analyse the latter at a specific wave length; in particular, this compound contributes towards destroying the resistant membranes of the red globules.

The saponins, which are also known as saponosides, are glycosides which have the capacity to lyse the erythrocytes specifically, but this lysis is less fast than that which is obtained in the presence of ionic detergents. When the saponins are used in association with other detergents, they make it possible to obtain faster, more specific lysis of the erythrocytes, which limits the deterioration of the leukocytes.

In addition, the chemical structure of this type of compound, which is characterised by multiple-ring carbon networks, permits physical and chemical stabilization of the oxidation derivatives of the haemoglobin.

The inorganic salt intervenes in the detergent activity. In addition, it is necessary in order to be able to carry out measurement by resistivity.

The osmotic agent plays substantially a leuko-protective role, when the reagent is used with a neutral pH, in order to assist differentiation of the leukocyte sub-populations.

Finally, the buffer is a key constituent, since the pH of the reagent is an important characteristic. In fact, according to the value of the pH, the reagent permits identification of one or a plurality of leukocyte sub-populations.

When the pH of the reagent is adjusted to a substantially neutral value (pH between 5 and 8), it is possible to quantify and identify the following three leukocyte sub-populations: lymphocytes, monocytes and neutrophils.

When the pH of the reagent is adjusted to a basic value (pH between 8 and 12), in addition it makes it possible to identify the polynuclear eosinophils.

Thus, for applications which require identification of the polynuclear eosinophils, it is necessary to adjust the pH of the reagent to a basic value.

On the other hand, if identification of the eosinophils is not required, the pH of the reagent is adjusted to a value which is substantially neutral.

In the reagent according to the invention, the detergent is advantageously selected from amongst the following components:
 the primary amines, acetates and hydrochiorates of fatty amines;
 the salts of quaternary ammonium, and the bromide of trimethylketyl ammonium;
 the amides of substituted diamines, which are rendered cationic by ethyl sulphate, diethanolamino-propylamine, diethylamino-propylamide; and
 the amides of ring-formed diethylenetriamine.

The detergent is advantageously present in a concentration of between 0 and 50 g/l, and more specifically, approximately 18 g/l.

From amongst the compounds of the glycoside type, preference is give in particular to the saponins, which are also known as saponosides, and can be either triterpenic or steroidal.

In the reagent according to the invention, the compound of the glycoside type is advantageously present in a concentration of between 0.5 and 20 g/l, and more specifically approximately 2 g/l.

The inorganic salt is advantageously selected from amongst the following compounds: chloride, sulphate or fluoride of sodium or potassium.

This inorganic salt is advantageously present in a concentration of between 1 and 15 g/l, and more specifically, approximately 8 g/l.

The osmotic and/or leuko-protective agent of the reagent according to the invention is advantageously selected from amongst mannitol, D-glucose and similar compounds.

This osmotic and/or leuko-protective agent is advantageously present in a concentration of between 0 and 30 g/l, and more specifically, approximately 2.5 g/l.

The organic and/or inorganic buffer is advantageously selected from amongst the following compounds:

triethanolamine;

hydrogenated phosphates of sodium and potassium;

N-[2-acetamido]-2 iminodiacetic acid;

N-[carbamoylmethyl] iminodiacetic acid;

2 amino-2-methyl 1,3 propanediol;

glycine;

sodium carbonate;

citric acid; and tris (hydroxymethyl) aminomethane.

This buffer is advantageously present in a concentration of between 0 and 2 wt. %.

According to a first embodiment of the invention, the buffer adjusts the pH of the reagent to a value of between 5 and 8.

According to another embodiment, this buffer adjusts the pH of the reagent to a value of between 8 and 12.

The invention is further described with reference to the following non-limiting examples.

EXAMPLE 1

A reagent is prepared from the following compounds, and in the concentrations indicated:

| Compounds | Concentration |
| --- | --- |
| Sodium chloride | 9 g/l |
| C15 H34 NCl (cationic detergent) | 12 g/l |
| Triterpenic saponin | 2 g/l |
| Sodium carbonate (buffer) | 2 g/l (0.2 wt. %) |

The compounds are mixed, and the pH is adjusted to a basic value of between 8 and 12, i.e. 10.5.

By means of the reagent thus prepared, two haematological analyses are carried out, using an automatic haematology device sold under the name ABX-Micros, made by the French company ABX.

For this purpose, a specific volume of the sample of blood to be analysed is previously mixed with specific volumes of a diluting agent, and of the aforementioned reagent.

Figure 2:
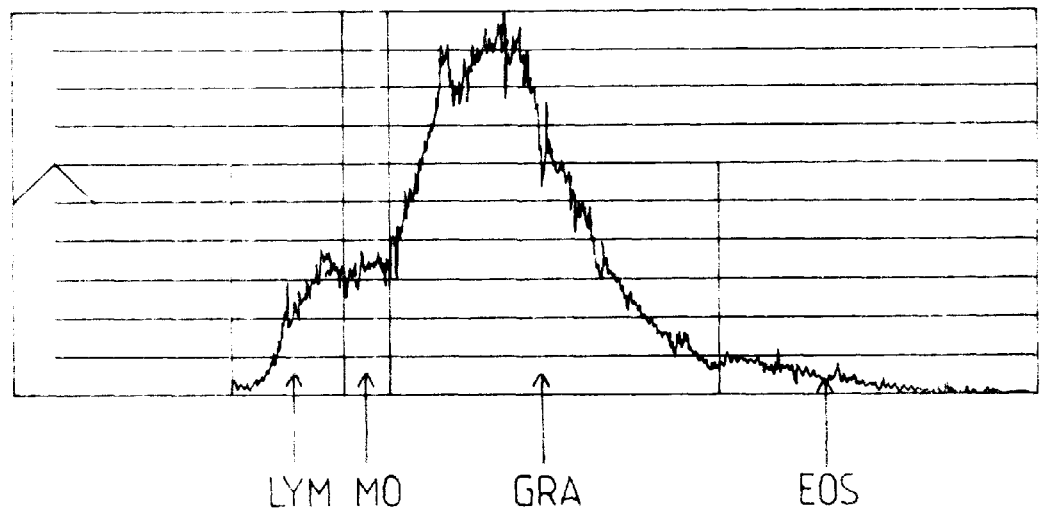

In the example, measurements are made on animal blood. The results of the measurements carried out on two different blood samples are shown in FIGS. 1 and 2.

These figures show the number of leukocytes, according to a relative intensity. The existence of 4 leukocyte sub-populations is found.

The figures relate to a resistive analysis, such that the following sub-populations can be seen from right to left, delimited by arrows: lymphocytes (LYM), monocytes (MO), granulocytes (GRA), and polynuclear eosinophils (EOS).

The automatic device provides the following measurement results, which indicate the number of cells counted, and the corresponding percentage, for each leukocyte sub-population.

| ANALYSIS 1 (FIG. 1) | | |
|---|---|---|
| LYM: | 3956 cells | 53.23% |
| MO: | 420 cells | 5.65% |
| GRA: | 2576 cells | 34.65% |
| EOS: | 481 cells | 6.47% |

| ANALYSIS 2 (FIG. 2) | | |
|---|---|---|
| LYM: | 1071 cells | 9.34% |
| MO: | 805 cells | 7.00% |
| GRA: | 8906 cells | 77.52% |
| EOS: | 706 cells | 6.14% |

Thus, the reagent according to the present example makes it possible to identify and quantify each of the four above-described sub-populations.

EXAMPLE 2

The same reagent as in example 1 is used, and similar analyses are carried out on two different samples of human blood. The measurements are made by means of an automatic ABX-Véga haematology device, made by the company ABX.

Figure 3:
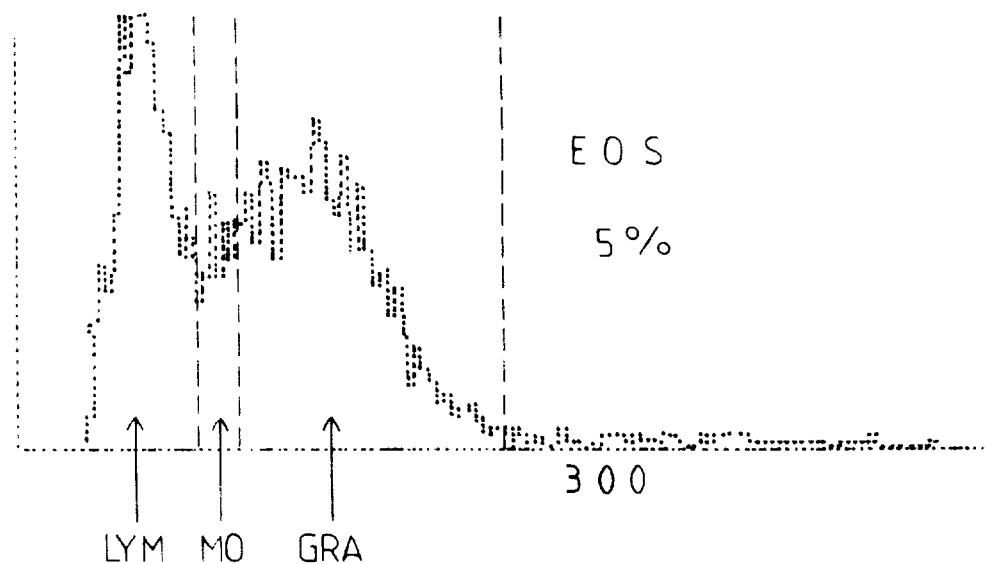
Figure 4:
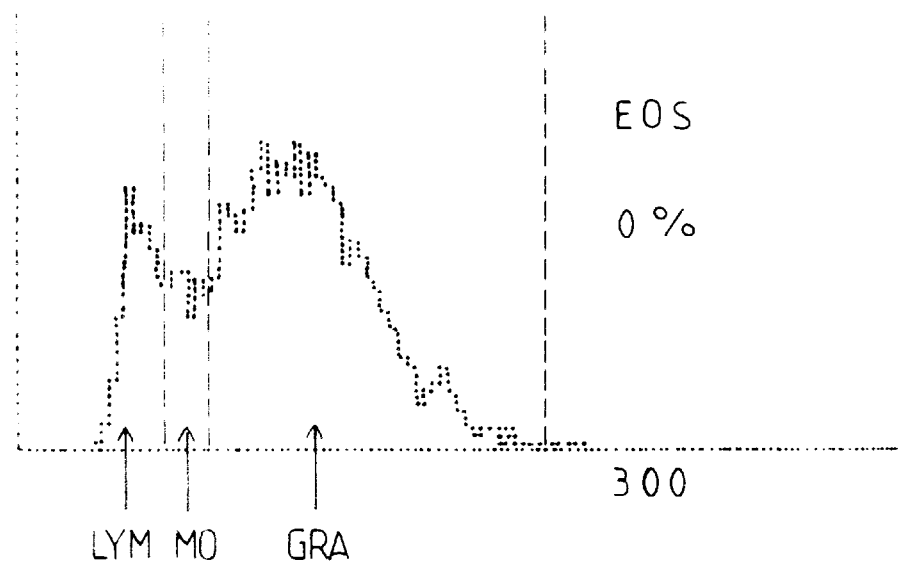

The results are shown in FIGS. 3 and 4.

For the sample which corresponds to FIG. 3, the analysis makes it possible to identify and quantify the following four sub-populations: lymphocytes (LYM), monocytes (MO), granulocytes (GRA), and polynuclear eosinophils (EOS). The latter represent 5% of the total population.

In the case of the sample which corresponds to FIG. 4, the analysis makes it possible to identify and quantify the three following sub-populations: lymphocytes (LYM), monocytes (MO) and granulocytes (GRA). In addition, the analysis shows that the sample does not contain any polynuclear eosinophils (0% level).

EXAMPLE 3

A reagent which is similar to those in examples 1 and 2 is used, but is adjusted to a neutral pH, i.e. 7.6%. Similar analyses are carried out on a sample of human blood. The measurements are made by means of an automatic ABX-Véga haematology device, made by the company ABX.

Figure 5:
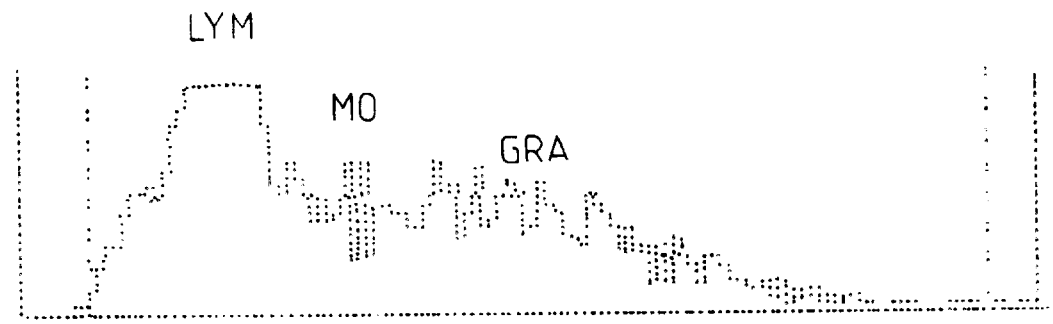

The results of the measurements are shown in FIG. 5. Only the following three main leukocyte sub-populations are detected: lymphocytes (LYM), monocytes (MO), and granulocytes (GRA).

EXAMPLE 4

A reagent similar to that in example 3 is used, which is therefore adjusted to a neutral pH. Similar analyses are carried out on a sample of human blood. The measurements are carried out by means of an automatic haematology device of the ABX-Micros type, made by the company ABX.

Figure 6:
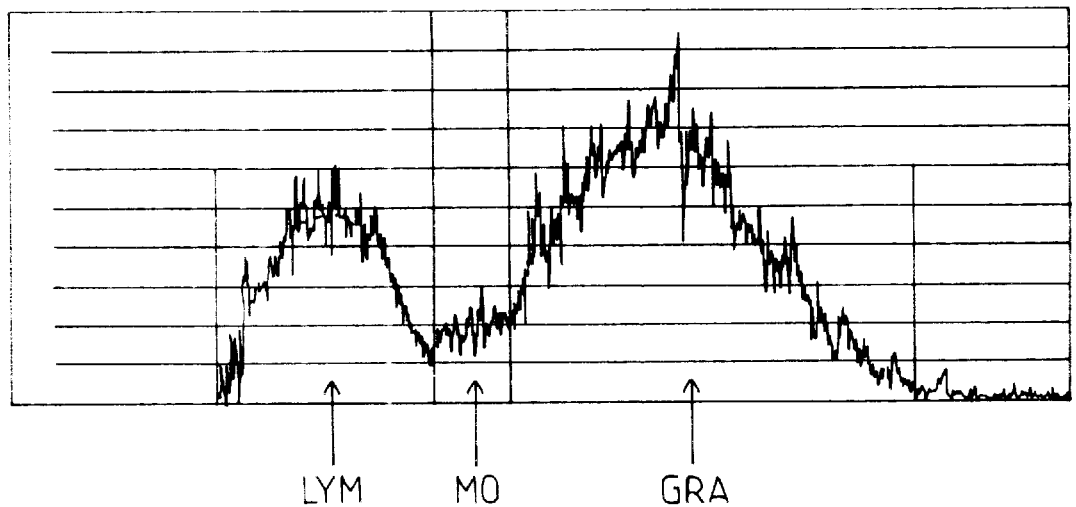

The results of the measurements are shown in FIG. 6. As in example 3, only the following three main leukocyte sub-populations are detected: lymphocytes (LYM), monocytes (MO), and granulocytes (GRA).

What is claimed is:

1. A reagent for measurement of the haemoglobin and determination of the leukocytes in a blood sample, which comprises:

at least one detergent of the cationic type;

a compound of the glycoside type;

at least one inorganic salt and/or an osmotic and/or leuko-protective agent; and an organic and/or inorganic buffer, which can adjust selectively the pH of the reagent, either to a substantially neutral value of between 5 and 8, or to a basic value of between 8 and 12.

2. The reagent of claim 1, wherein the detergent is selected from the group consisting of:

the primary amines, acetates and hydrochlorates of fatty amines;

the salts of quaternary ammonium, and the bromide of trimethylketyl ammonium;

the amides of substituted diamines, which are rendered cationic by ethyl sulphate, diethanolaminopropylamine, diethylamino-propylamide; and the amides of ring-formed diethylenetriamine.

3. The reagent of claim 2, wherein the detergent is present in a concentration of between 0 and 50 g/l.

4. The reagent of claim 1, wherein the compound of the glycoside type is selected from the group consisting of saponins and saponosides.

5. The reagent of claim 1, wherein the glycoside compound is present in a concentration of between 0.5 and 20 g/l.

6. The reagent of claim 1, wherein the inorganic salt is selected from the group consisting of chloride, sulphate or fluoride of sodium and potassium.

7. The reagent of claim 1, wherein the inorganic salt is present in a concentration of between 1 and 15 g/l.

8. The reagent of claim 1, wherein the osmotic and/or leuko-protective agent is selected from the group consisting of mannitol and D-glucose.

9. The reagent of claim 1, wherein the osmotic and/or leuko-protective agent is present in a concentration of between 0 and 30 g/l.

10. The reagent of claim 1, wherein the organic and/or inorganic buffer is selected from the group consisting of:

triethanolamine;

hydrogenated phosphates of sodium and potassium;

N-[2-acetamido]-2 iminodiacetic acid;

N-[carbamoylmethyl] iminodiacetic acid;

2 amino-2-methyl 1,3 propanediol;

glycine;

sodium carbonate;

citric acid; and tris (hydroxymethyl) aminomethane.

11. The reagent of claim 1, wherein the organic and/or inorganic buffer is present in a concentration of between 0 and 2 wt. %.

12. The reagent of claim 1, wherein the buffer adjusts the pH of the reagent to a value of between 5 and 8.

13. The reagent of claim 1, wherein the buffer adjusts the pH of the reagent to a value of between 8 and 12.

14. The reagent of claim 1 being free of cyanide compounds.

* * * * *